United States Patent [19]

Ghosh et al.

[11] 4,370,333

[45] * Jan. 25, 1983

[54] 17-CYCLOPROPYLMETHYL-3-HYDROXY-14-METHOXY 7α-METHYL-MORPHINAN-6-ONE AND THERAPEUTIC METHOD OF TREATING PAIN WITH IT

[75] Inventors: Anil C. Ghosh, Lexington; Raj K. Razdan, Belmont, both of Mass.

[73] Assignee: SISA, Incorporated, Cambridge, Mass.

[*] Notice: The portion of the term of this patent subsequent to Jun. 9, 1998, has been disclaimed.

[21] Appl. No.: 278,760

[22] Filed: Jun. 29, 1981

[51] Int. Cl.³ .................. A61K 31/485; C07D 221/28
[52] U.S. Cl. ..................................... 424/260; 546/74
[58] Field of Search .......................... 546/74; 424/260

[56] References Cited

U.S. PATENT DOCUMENTS

| | | | |
|---|---|---|---|
| 3,654,280 | 4/1972 | Sawa et al. | 546/74 |
| 4,230,712 | 10/1980 | Kotick et al. | 424/260 |
| 4,272,540 | 6/1981 | Razdan et al. | 424/260 |

Primary Examiner—Donald G. Daus
Assistant Examiner—Diana G. Rivers
Attorney, Agent, or Firm—Jerome L. Jeffers

[57] ABSTRACT

Disclosed is the novel analgesic/narcotic antagonist 17-cyclopropylmethyl-3-hydroxy-14-methoxy-7α-methyl-morphinan-6-one.

6 Claims, No Drawings

17-CYCLOPROPYLMETHYL-3-HYDROXY-14-METHOXY 7α-METHYL-MORPHINAN-6-ONE AND THERAPEUTIC METHOD OF TREATING PAIN WITH IT

BACKGROUND OF THE INVENTION

1. Field of the Invention

Morphine is a well known narcotic analgesic having the structural formula:

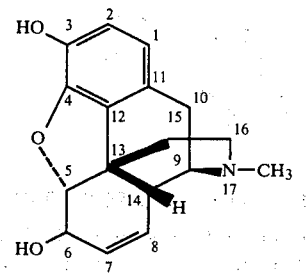

The compound of this invention is structurally related to morphine and is named according to the morphinan system of nomenclature using the morphinan nucleus which is shown below:

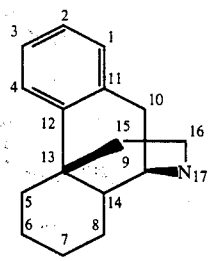

The numbering and stereochemical placement of atoms in the morphinan system is the same as that depicted for morphine. A dashed line is used to represent a covalent bond projecting below the plane of a reference atom while a wedged or heavily accented line signifies a covalent bond above such plane. The compound of this invention has the same stereochemical placement of atoms as depicted for morphine.

Morphine and its structurally related relatives are used primarily as analgesics. While extremely effective for the relief of moderate to severe pain these compounds are narcotic and most possess dependence-inducing ability and produce other side effects such as emesis, constipation, sweating, respiratory depression and myosis which make them less than ideal analgesics. It is impossible to predict, based on structure alone, whether a particular morphine-like compound will act as an analgesic (agonist), a narcotic antagonist or possess a combination of these properties since very minute structural modifications in the molecule can significantly change the way it affects an individual to which it is administered. A compound with the appropriate profile of analgesic (agonist) and narcotic antagonist actions has potential for treatment of moderate to severe pain without the liability of drug dependence or drug abuse. The compound of the present invention is a potent mixed analgesic/narcotic antagonist with an acceptable ratio of analgesic activity to narcotic antagonist activity.

2. Prior Art

Morphinans which are hydroxy substituted in the 14-position are known. Thus, I. J. Pachter reports in *Narcotic Antagonists, Advances in Biochemical Psychopharmacology*, Vol. 8, Raven Press, New York 1973, p. 57, the preparation of compounds having the structure:

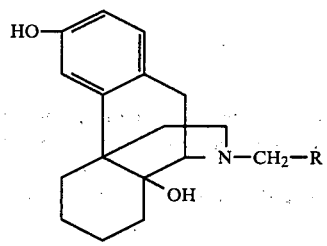

where R is cyclopropyl (A) or cyclobutyl (B). The compound in which R is cyclopropyl is reported to be essentially a narcotic antagonist while that compound in which R is cyclobutyl is reported to possess both analgesic and narcotic antagonist activity. This article also reports the preparation by the Shionogi Company in Japan of a compound having the formula:

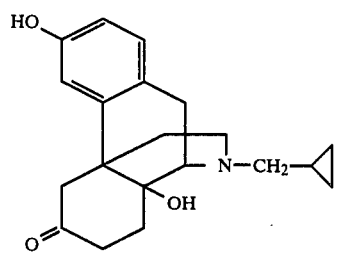

It is stated that this compound is very long acting and more potent than (A) (above), cyclazocine or naloxone. Naloxone is a potent narcotic antagonist whereas cyclazocine has mixed analgesic/narcotic antagonist activity. This compound was found to have analgesic activity (designated as $ED_{50}$) of 2.2 mg./kg. and narcotic antagonist activity (designated as $AD_{50}$) of 0.082 mg./kg.

Compounds of the general formula:

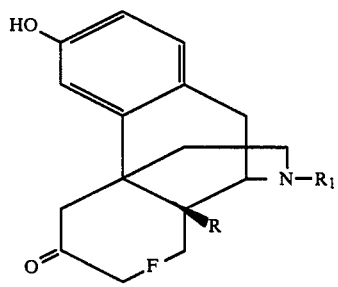

where R is a hydrogen atom or hydroxyl group; $R_1$ is allyl, γ,γ-dimethylallyl or cyclopropylmethyl; and F represents the presence or absence of a double bond are disclosed in U.S. Pat. No. 3,654,280 which issued Apr. 4, 1972.

A compound of the formula:

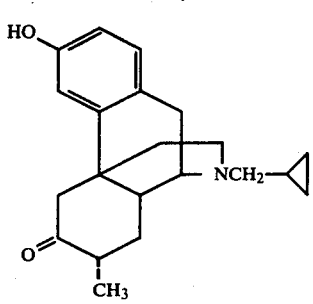

is disclosed in European Patent Bulletin number 1980/24 under the publication number 0019254. The compound is described as having analgesic activity of 9.87 mg./kg. and narcotic antagonist activity of 5.2 mg./kg.

SUMMARY OF THE INVENTION

The present invention is 17-cyclopropylmethyl-3-hydroxy-14-methoxy-7α-methylmorphinan-6-one characterized by the structural formula:

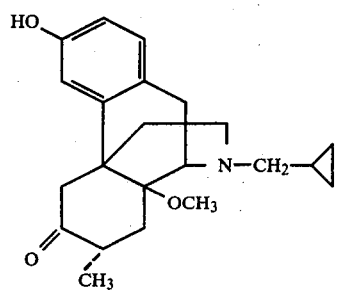

DETAILED DESCRIPTION

The preparation of the compound of the present invention is schematically set out in Scheme I.

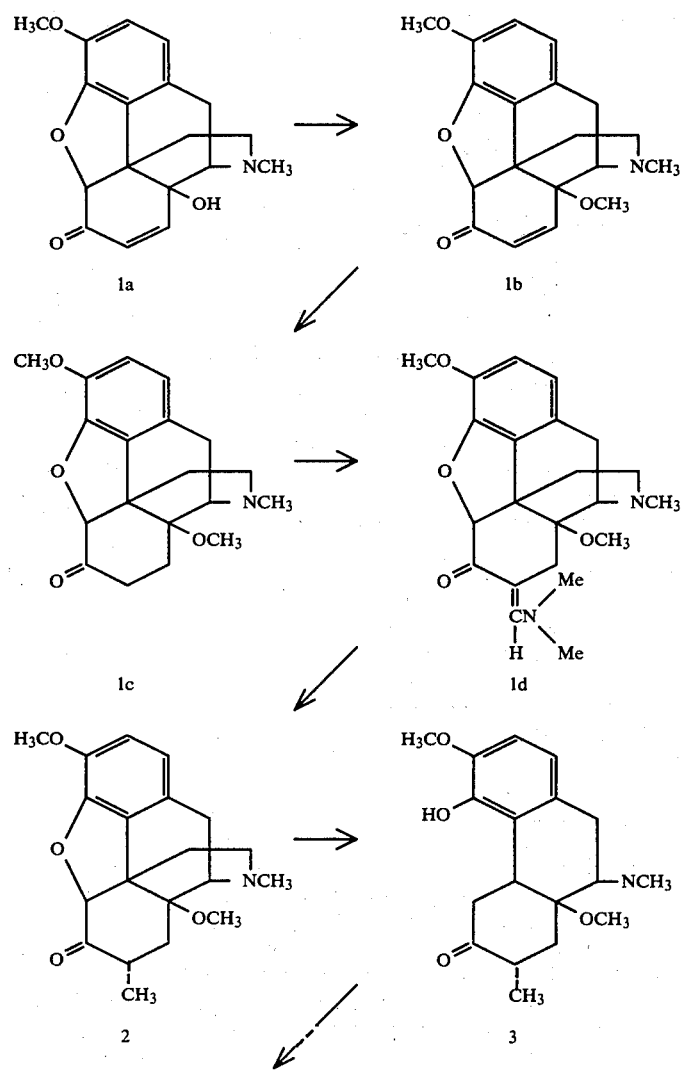

SCHEME I

SCHEME I

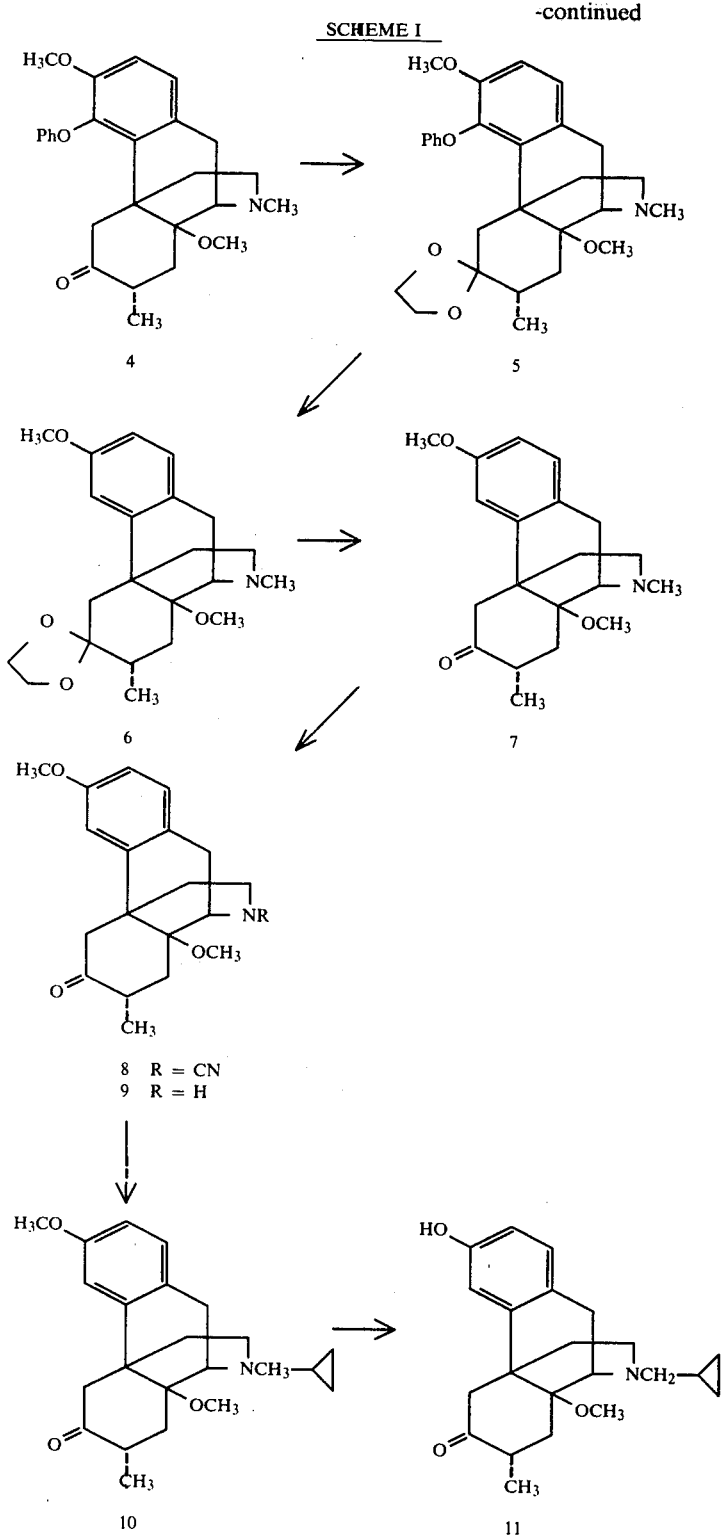

8 R = CN
9 R = H

Referring to Scheme I, Compound 1a (14-hydroxycodeinone) is treated with methyl iodide and sodium hydride to give 14-methoxycodeinone, Compound 1b. Compound 1c is obtained when 1b is hydrogenated in the presence of a catalyst such as 10% palladium on charcoal. Treatment of Compound 1c with dimethylformamide dimethyl acetal gives Compound 1d, which is subsequently hydrogenated in the presence of a catalyst such as 10% palladium on charcoal to give the 7α methyl substituted Compound 2. The 4,5α-epoxy group of Compound 2 is opened by first treating with a mixture of zinc dust, ammonium chloride and alcohol to give Compound 3. The 4-hydroxy group of Compound 3 is converted to the corresponding 4-phenoxy of 4 by reacting with bromobenzene. Prior to removal of the phenoxy group by treatment with sodium/liquid ammonia to give Compound 6, the oxo group in the 6-position of Compound 4 is protected as the ethylene glycol ketal (Compound 5). The protecting ketal group of 6 is removed by heating with dilute acid to give Compound 7. Treatment of 7 with cyanogen bromide, followed by acid hydrolysis, gives Compound 9, which is reacted with cyclopropylmethyl bromide in a suitable inert solvent and in the presence of a base. Dimethylformamide and sodium bicarbonate have been used. Compound 11 is obtained when 10 is treated with boron tribromide in an inert solvent to selectively demethylate the methoxy in the 3-position, while leaving the 14-methoxy unchanged.

This preparation is more fully described in the following example:

A.
7,8-didehydro-4,5α-epoxy-14-hydroxy-3-methoxy-17-methylmorphinan-6-one (1a) (14-hydroxycodeinone)

This compound was prepared by the method of Hauser et al, *J.Med.Chem.*, 17, 1117 (1974).

B.
7,8-didehydro-3,14-dimethoxy-4,5α-epoxy-17-methylmorphinan-6-one (1b)

To a suspension of sodium hydride (57% oil dispersion, 13.5 g., 0.319 mol) in 30 ml. of dimethylformamide under nitrogen was added a solution of 14-hydroxycodeinone (1a) (25 g., 79.8 mmol) in 450 ml. of DMF. The mixture was stirred at room temperature for 1 hour and cooled in an ice bath whereupon methyl iodide (15.5 g., 0.109 mol) was added dropwise and the mixture was allowed to warm up to room temperature. Stirring was continued for another 3 hours and at the end of this period the excess sodium hydride was decomposed very cautiously by the dropwise addition of water. Most of the DMF was removed by vacuum distillation (oil bath temperature 35°-40° C.) and the residue was taken up in 400 ml. of methylene chloride. The organic layer was washed with water (3×100 ml.), saturated sodium chloride solution (2×100 ml.) and again with water (3×100 ml.). The aqueous layer was re-extracted with methylene chloride (2×300 ml.) and the organic extracts were combined. After drying over MgSO$_4$ and filtration, the organic solution was concentrated under reduced pressure to give an orange-brown residue (19.7 g.). A solution of the residue in chloroform was passed through a column of Florisil (400 g.) and eluted with graded chloroform/benzene mixtures. The fractions containing Compound 14 were collected and the product was recrystallized from ethanol to give 13.6 g. (50% theory) of 14-methoxycodeinone (14) as a tan solid, 143°-144° C.

Analysis: NMR (CDCl$_3$) δ2.48 (s, 3H, N—CH$_3$), 3.28 (s, 3H, C$_{14}$—OCH$_3$), 4.73 (s, 1H, C$_5$—H) and 6.43-6.80 (m, 2H, aromatics). IR (CHCl$_3$) $\nu_{max}$ 1683 cm$^{-1}$ (>C=O).

Anal. Calcd. for C$_{19}$H$_{21}$NO$_4$: C, 69.70; H, 6.47; N, 4.28. Found: C, 69.73; H, 6.46; N, 4.17.

C.
3,14-Dimethoxy-4,5-epoxy-17-methylmorphinan-6-one (1c)

7,8-Didehydro-3,14-dimethoxy-4,5-epoxy-17-methylmorphinan-6-one (14) (5.0 g., 15.27 mmol) was hydrogenated in methanol (75 ml.) over 500 mg. Pd/charcoal (10%) at 3 atm. After filtration through Celite the solvent was removed under reduced pressure to afford 4.92 g. (98% theory) of a white solid 15, mp 140°-142° C. Recrystallization from ethanol gave 4.52 g. (90% theory) of 15 as a white solid, mp 146°-146.5° C.

Analysis: NMR (CDCl$_3$) δ2.40 (s, 3H, N—CH$_3$), 3.33 (s, 3H, C$_{14}$—OCH$_3$), 3.88 (s, 3H, C$_3$OCH$_3$), 4.6 (s, 1H, C$_5$—H), 6.65 (s, 2H, aromatics). IR (CHCl$_3$) $\nu_{max}$ 1720 cm$^{-1}$ (>C=O).

Anal. Calcd. for C$_{19}$H$_{23}$NO$_4$: C, 69.27; H, 7.05; N, 4.25. Found: C, 69.27; H, 7.02; N, 4.21.

D.
3,14-Dimethoxy-7-N,N-dimethylaminomethylene-4,5α-epoxy-17-methylmorphinan-6-one A solution of 1c (24.00 g., 73.17 mmol) in toluene (50 ml.) was treated with dimethylformamide dimethyl acetal (87.22 g., 731.7 mmol) and the mixture was refluxed under stirring and N$_2$ atmosphere for 72 hr. The yellow precipitate formed was then filtered and washed with toluene (2×50 ml.). This was dried in vacuo to give 22.68 g. (81%) of 1d as yellow needles, m.p. 286°-287° C. TLC shows a single spot (Rf 0.54, 20% methanol in chloroform).

NMR (CDCl$_3$) δ6.63 (s, 2H, Ar—H), 4.57 (s, 1H, H5), 3.83 (s, 3H, C$_3$—OCH$_3$), 3.27 (s, 3H, C$_{14}$—OCH$_3$), 3.03 (s, 6H, N(CH$_3$)$_2$) and 2.40 (s, 3H, N—CH$_3$).

E.
3,14-Dimethoxy-7α,17-dimethyl-4,5α-epoxymorphinan-6-one (2)

A solution of 1d (22.60 g., 58.85 mmol) in methanol (1 liter) was hydrogenated at 50 psi with 10% Pd/C (4.0 g.) for 3 days. The solution was filtered through Celite, and the solvent was removed in vacuo to give 19.34 g. (95%) of 2, m.p. 215°-221° C. TLC showed a single spot (Rf 0.63, 20% methanol in chloroform).

NMR (CDCl$_3$) δ6.60 (s, 2H, Ar—H), 4.63 (s, 1H, H5), 3.90 (s, 3H, C$_3$OCH$_3$), 3.33 (s, 3H, C$_{14}$—OCH$_3$), 2.40 (s, 3H, N—CH$_3$) and 0.94 (d, J=7 Hz, 3H, 7α—CH$_3$).

F.
3,14-Dimethoxy-7α,17-dimethyl-4-hydroxymorphinan-6-one (3)

A solution of 2 (3.72 g., 10.8 mmol) in absolute ethanol (75 ml.) was treated with zinc dust (4.95 g., 75.7 mmol) and ammonium chloride (4.63 g., 85.6 mmol) and the mixture was refluxed overnight under stirring and N$_2$ atmosphere. The reaction mixture was filtered under suction and the ethanol removed in vacuo. The residue was taken up in water (150 ml.) and chloroform (100 ml.). The aqueous layer was made basic (pH 10.5) with ammonium hydroxide. The chloroform layer was removed and the aqueous layer extracted with chloroform (100 ml.) and ethyl acetate (2×150 ml.). The organic extracts were combined and dried over sodium sulfate. The solvents were removed in vacuo to give 3.20 g. (86%) of 3. This gave a single spot on thin-layer chromatography (Rf 0.27, 20% methanol in chloroform). The NMR and MS analysis was conducted on the free base whereupon the compound was converted to its HCl salt for elemental analysis.

NMR (CDCl$_3$) δ6.60 (s, 2H, Ar—H), 3.80 (s, 3H, C$_3$—OCH$_3$), 3.38 (s, 3H, C$_{14}$—OCH$_3$), 2.37 (s, 3H, N—CH$_3$) and 0.88 (d, J=6 Hz, 3H, 7α—CH$_3$). IR (KBr), $\nu_{max}$ 1710 cm$^{-1}$ (>C=O).

MS m/e 346 (M$^+$), 315 (M$^+$−31).

Anal. Calcd. for C₂₀H₁₇NO₄.HCl (mol.wt. 381.9); C, 62.90; H, 7.34; N, 3.67; Cl, 9.28. Found: C, 62.78; H, 7.47; N, 3.67; Cl, 9.18.

G. 3,14-Dimethoxy-7α,17-dimethyl-4-phenoxy morphinan-6-one (4)

Potassium carbonate (2.70 g., 1.95 mmol) was dried in a vacuum oven at 110° C. for 2 hours, and added to a solution of 3 (5.00 g., 14.45 mmol) in pyridine (50 ml.). The mixture was stirred for 10 minutes under a N₂ atmosphere, and a solution of bromobenzene (2.57 g., 16.37 mmol) in pyridine (20 ml.) was added followed by copper (0.250 g., 3.94 mmol) powder. The reaction mixture was stirred overnight at reflux, under an N₂ atmosphere. More copper powder (0.100 g., 1.57 mmol) was added, and the reaction was continued for another 24 hours. The mixture was filtered under suction, and the pyridine was removed in vacuo, to give 6.43 g. of a dark residue. This was chromatographed on a column of silica gel (150 g., 100-200 mesh), with a gradient solvent mixture of 0 to 20% methanol in chloroform as eluant, to give 4.79 g. (78%) of 4.

The sample gave a single spot on thin-layer chromatography (Rf 0.35, 20% methanol in chloroform). The NMR and MS analysis was conducted on the free base whereupon the compound was converted to its HCl salt for elemental analysis.

NMR (CDCl₃) δ6.97 (m, 7H, Ar—H), 3.57 (s, 3H, C₃—OCH₃), 3.35 (s, 3H, C₁₄—OCH₃), 2.35 (s, 3H, N—CH₃) and 0.87 (d, J=6 Hz, 3H, 7α—CH₃). IR(KBr), $\nu_{max}$ 1705 cm⁻¹ (>C=O). MS m/e, 421 (M+), 390 (M+ −31).

Anal. Calcd. for C₂₆H₃₁NO₄.HCl.H₂O (mol.wt. 476.00): C, 65.66; H, 7.11; N, 2.96; Cl, 7.52. Found: C, 65.60; H, 7.20; N, 2.94; Cl, 7.45.

H. 3,14-Dimethoxy-7α,17-dimethyl-4-phenoxymorphinan-6-one ethylene glycol ketal (5)

A mixture of 4 (12.30 g., 29.15 mmol) benzene (250 ml.), p-toluenesulfonic acid (13.26 g., 69.79 mmol) and ethylene glycol (50 ml., 1.08 mole) was refluxed under stirring for 6 hours. The water formed was removed azeotropically, using a Dean Stark apparatus. The reaction mixture was stirred at room temperature overnight, and was then placed in a separatory funnel. The benzene layer was removed, and the lower layer was made basic (pH 9.0) with a 10% sodium carbonate solution. This was then extracted with benzene (2×75 ml.). The benzene layers were combined, and washed with 10% sodium carbonate (200 ml.) and water (200 ml.). The benzene layer was dried with sodium sulfate, and the solvent removed in vacuo to give 13.34 g. (98.2%) of 5. This gave a single spot on thin-layer chromatography (Rf 0.29, 20% methanol in chloroform).

NMR (CDCl₃) δ6.92 (m, 7H, Ar—H), 3.63 (s, 3H, C₃OCH₃), 3.20 (s, 3H, C₁₄—OCH₃), 2.37 (s, 3H, N—CH₃) and 0.78 (d, J=6 Hz, 3H, 7α-CH₃). IR (KBr) indicated the absence of carbonyl absorption.

I. 3,14-Dimethoxy-7α,17-dimethylmorphinan-6-one ethylene glycol ketal (6)

A solution of 5 (8.00 g., 1717 mmol) in tetrahydrofuran (250 ml.) was added to freshly distilled liquid ammonia (400 ml.), over a period of 30 min. Sodium (2.70 g., 117.4 mmol) was washed in toluene, and slowly added to the reaction mixture in small pieces. The blue solution was stirred for 30 min., and ammonium chloride was then added in small portions until the blue color disappeared. Water (2.0 ml.) was slowly added, and the ammonia was allowed to evaporate at room temperature overnight. The reaction mixture was diluted with diethyl ether (150 ml.), and this was washed with 5% sodium hydroxide (200 ml.), and water (200 ml.). The ether layer was dried with sodium sulfate and the solvents removed in vacuo to give 5.80 g. of a crude mixture containing 6.

J. 3,14-Dimethoxy-7α,17-dimethylmorphinan-6-one (7)

A solution of 6 (5.80 g., 15.5 mmol) in 5% HCl (150 ml.) was stirred at reflux for 90 min. The reaction mixture was then cooled to room temperature and extracted with methylene chloride (3×150 ml.). The organic extracts were combined, dried with sodium sulfate, and the solvents removed in vacuo to give 4.93 g. (96%) of 7. This material gave a single spot on thin-layer chromatography (Rf 0.69, 20% methanol in chloroform).

NMR (CDCl₃) δ6.80 (m, 3H, Ar—H), 3.73 (s, 3H, C₃—OCH₃), 3.40 (s, 3H, C₁₄—OCH₃), 2.40 (s, 3H, N—CH₃) and 0.84 (d, J=7 Hz, 2H, 7α—CH₃). IR (KBr), $\nu_{max}$ 1710 cm⁻¹ (>C=O). MS m/e 329 (M+).

K. 17-Cyano-3,14-dimethoxy-7α-methylmorphinan-6-one (8)

A solution of 7 (12.00 g., 36.32 mmol) in methylene chloride (300 ml.) was stirred at reflux overnight with cyanogen bromide (22.00 g., 207.5 mmol) and sodium carbonate (27.00 g., 207.5 mmol). The reaction mixture was filtered with suction, and the solvent removed in vacuo to give 11.80 g. (95%) of 8. This material was used in the next step without purification.

L. 3,14-Dimethoxy-7α-methylmorphinan-6-one (9)

A solution of 8 (11.80 g., 34.56 mmol) in 2 N HCl (300 ml.) was stirred at reflux for 7 hours. It was then cooled to room temperature, and left to stir overnight. The reaction mixture was then placed in a separatory funnel and made basic (pH 10.0) with ammonium hydroxide. This was then extracted with methylene chloride (3×100 ml.). The organic extracts were combined, dried with sodium sulfate, and the solvent evaporated to give 11 g. of crude 9.

NMR (CDCl₃) δ6.87 (m, 3H, Ar—H), 3.75 (s, 3H, C₃—OCH₃), 3.40 (s, 3H, C₁₄—OCH₃) and 0.84 (d, J=7 Hz, 3H, 7α—CH₃). IR (KBr) $\nu_{max}$ 1710 cm⁻¹ (>C=O).

M. 17-Cyclopropylmethyl-3,14-dimethoxy-7α-methylmorphinan-6-one (10)

A mixture of 9 (5.00 g., 15.80 mmol) in dimethylformamide (150 ml.), cyclopropylmethyl bromide (4.80 g., 31.61 mmol) and sodium bicarbonate (5.31 g., 63.21 mmol) was stirred overnight under N₂ atmosphere at room temperature. The solid was then removed by suction filtration, and the filtrate vacuum distilled to give 6.53 g. red oil. This was chromatographed on a column of silica gel (230-400 mesh, 120 g.) with a gradient solvent mixture of 0 to 10% methanol in chloroform, to give 4.26 g. (73%) of 10.

NMR (CDCl₃) δ6.82 (m, 3H, Ar—H), 3.77 (s, 3H, C₃OCH₃), 3.45 (s, 3H, C₁₄OCH₃) and 0.85 (d, J=6 Hz, 3H, 7α—CH₃). IR (KBr) $\nu_{max}$ 1710 cm⁻¹ (>C=O). MS m/e 369 (M+).

N.
17-Cyclopropylmethyl-3-hydroxy-14-methoxy-7α-methyl-morphinan-6-one (11)

A solution of boron tribromide (3.43 g., 13.53 mmol) in chloroform (10 ml.) was cooled in an ice bath. To this was added a solution of 11 (0.500 g., 1.353 mmol) in chloroform (10 ml.) over 1 min. The solution was stirred at 0° C. under an $N_2$ atmosphere for 2 hours. Methanol (25 ml.) was then added over 10 min. The ice bath was removed, and the reaction mixture stirred at room temperature overnight. The reaction mixture was dried in vacuo to give an orange foam (0.638 g.). This was taken up in water (75 ml.) and methylene chloride (175 ml.), and placed in a separatory tunnel. The aqueous layer was made basic (pH 10.0) with ammonium hydroxide. The methylene chloride layer was removed, and the aqueous layer was again extracted with methylene chloride (3×75 ml.). The organic extracts were combined, dried with sodium sulfate, and solvents removed in vacuo to give a white foam (0.5 g.). This was chromatographed on a silica gel column (63-200 mesh, 20 g.) with chloroform as eluant to give 0.413 (86%) of 11.

NMR (CDCl$_3$) δ6.75 (m, 3H, Ar—H), 3.43 (s, 3H, C$_{14}$—OCH$_3$) and 0.88 (d, J=6 Hz, 3H, 7α-CH$_3$). IR (KBr) $\nu_{max}$ 1710 cm$^{-1}$ (>C=O). MS m/e 355 (M+), 324 (M+−31), 314 (M+−41).

Anal. Calcd. for $C_{22}H_{29}NO_3$ (mol.wt. 355.5): C, 72.49; H, 8.30; N, 3.84. Found: C, 72.59; H, 8.34; N, 3.49.

PHARMACOLOGICAL EVALUATION

The compound whose preparation is disclosed in the foregoing example was screened to determine the following biological activities:
(A) Analgesic effects upon mice (acetic acid writhing test).
(B) Narcotic antagonist activity in rats (modified rat tail flick test).

TEST A. ACETIC ACID MOUSE WRITHING TEST

The analgesic effects of the test compound was determined in mice by use of the acetic acid writhing test described by B. A. Whittle, Brit.J.Pharmacol., 22:246 (1964). In this test at least three groups of five mail CD-1 mice each were given subcutaneous doses of the test drug dissolved in either distilled water or distilled water acidified with HCl depending on the solubility of the compound. Fifteen (15) min. post drug, 0.6 milliliter of a 1.0% V/V acetic acid in distilled water solution was administered intraperitoneally. The number of writhes in a 20 min. interval beginning 5 min. after the acetic acid injection were determined and compared with the number of writhes in control groups which had received only acetic acid.

Percent inhibition of writhing was calculated as:

$$\% \text{ inhibition} = \frac{\text{No. control writhes} - \text{No. treated writhes}}{\text{No. control writhes}} \times 100$$

The ED$_{50}$ dose, i.e., the dose required to reduce the number of writhes by 50%, was determined graphilog dose. Confidence limits of 95% were calculated on the basis of those results falling in the range 16-84% inhibition. See Litchfield, J. T. and Wilcoxon, F., J.Pharmacol.Exp.Ther., 96:99, (1949).

TEST B. EVALUATION OF NARCOTIC ANTAGONIST ACTIVITY

The narcotic antagonist effects of the test compound was determined by a modification of the rat tail flick procedure of Harris and Pierson, J.Pharmacol.Exp.Ther. 143:141 (1964).

Male albino Wistar rats (100-120 g.) were used for this study. A rat's tail is so placed so as to cover a photocell. Heat is applied by a lamp in a reflector with a timer being connected to the lamp and photocell so that the timer goes on when the light is turned on and is turned off when the photocell is uncovered. A rheostat, incorporated into a heating lamp is used to adjust the intensity of the light falling on the tail of the rat such that the rat's control reaction time is from 1.2 to 4.1 seconds. Animals with a control reaction time outside this range are rejected. The rheostat adjustment is made only if a significant proportion (more than 1 out of every 10 rats) of the reaction times are outside the range of 2 to 4 seconds. Groups of five rats were used each time, and two control times were determined at least 30 min. apart.

The test drug was given intraperitoneally and this was followed 10 min. later by an ED$_{80}$ dose of morphine subcutaneously. The animals were retested at 20 min. after the morphine injection. Control animals were given morphine only. A 10 second cutoff time is employed; if the rat does not flick its tail in 10 seconds, it is removed from the heat source. The data was calculated as follows:

$$\% \text{ Effect } (E) = \frac{MRT^* \text{ (Treated)} - MRT \text{ (Control)}}{10 - MRT \text{ (Control)}} \times 100$$

$$\% \text{ Antagonism} = \frac{E \text{ (morphine controls)} - E \text{ (drug treated)}}{E \text{ (morphine control)}} \times 100$$

The data was plotted on log-probit paper and the AD$_{50}$ value, i.e., the dose required to inhibit the morphine effect by 50% within 95% confidence limits, was determined by the method of Litchfield and Wilcoxon.

The foregoing tests were used to determine that the ED$_{50}$/AD$_{50}$ values for the claimed compound were 0.96 mg./kg. and 0.84 mg./kg., respectively. From the foregoing data, it can be determined that this compound possesses mixed analgesic/narcotic antagonist activity and has a ratio of ED$_{50}$ to AD$_{50}$ of about 1. This compound has also been found to exhibit a novel action in the charcoal meal test upon attempted naloxone reversal. The compound is of special interest because it is useful for treating moderate to severe pain in an individual without the liability of drug dependence.

The term "individual" means a human being or an experimental animal that is a model for a human being. The dose to be administered to achieve the desired result, i.e., the effective dose, may vary from individual to individual but is readily determined by one skilled in the art without undue experimentation.

The compound of the present invention forms pharmacologically active addition salts which are normally preferred due to their increased water solubility and the resulting greater ease of administration. These compounds may be administered by known, conventional methods of therapeutic administration such as intravenous, parenteral, buccal, rectal or oral. Dose forms for the administration of these compounds can be prepared by methods recognized in the pharmaceutical sciences.

What is claimed is:

1. 17-Cyclopropylmethyl-3-hydroxy-14-methoxy-7α-methyl-morphinan-6-one characterized by the structural formula:

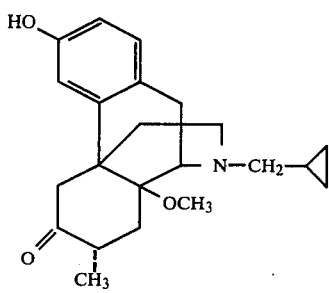

2. The compound as described in claim 1 in the form of its acid addition salt.

3. The compound as described in claim 2 in the form of its hydrochloride.

4. A therapeutic method for treating pain without liability of drug dependence in an individual for whom such therapy is indicated which method comprises administering to the individual an effective analgesic amount of a compound characterized by the formula:

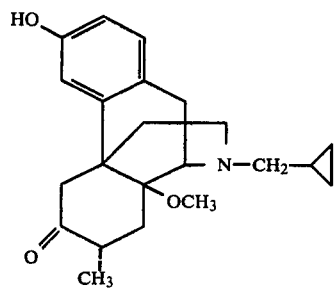

5. The method of claim 1 wherein the compound is in the form of its acid addition salt.

6. The method of claim 5 wherein the compound is in the form of its hydrochloride.

* * * * *